(12) United States Patent
Andreasson et al.

(10) Patent No.: US 7,003,073 B2
(45) Date of Patent: Feb. 21, 2006

(54) X-RAY DIAGNOSTIC DEVICE FOR MAMMOGRAPHY EXAMINATIONS

(75) Inventors: Jesper Andreasson, Järfälla (SE);
Stefan Karlsson, Sollentuna (SE);
Josefin Teksöz-Wibrink, Sundbyberg (SE)

(73) Assignee: Siemens Aktiengesellschaft, Munich (DE)

( * ) Notice: Subject to any disclaimer, the term of this patent is extended or adjusted under 35 U.S.C. 154(b) by 157 days.

(21) Appl. No.: 10/408,020

(22) Filed: Apr. 4, 2003

(65) Prior Publication Data

US 2003/0198315 A1    Oct. 23, 2003

(30) Foreign Application Priority Data

Apr. 23, 2002  (SE)  .................... 0201211

(51) Int. Cl.
*A61B 6/04* (2006.01)
(52) U.S. Cl. .................. 378/37; 378/177; 378/208
(58) Field of Classification Search .................. 378/37, 378/177, 208, 189, 190
See application file for complete search history.

(56) References Cited

U.S. PATENT DOCUMENTS

| 4,019,059 A | | 4/1977 | Brundin et al. | |
|---|---|---|---|---|
| 4,910,756 A | * | 3/1990 | Mikkonen et al. | ............. 378/37 |
| 4,979,196 A | | 12/1990 | Lieutaud et al. | |
| 5,170,420 A | * | 12/1992 | Warden | ........................ 378/37 |
| 6,459,925 B1 | * | 10/2002 | Nields et al. | ................ 600/427 |
| 6,785,578 B1 | * | 8/2004 | Johnson et al. | ............... 700/60 |

FOREIGN PATENT DOCUMENTS

| EP | 0 324 358 | 6/1992 |
|---|---|---|
| EP | 0 370 089 | 3/1994 |
| EP | 0 775 467 | 5/1997 |
| WO | WO 89/1124 | 11/1989 |

* cited by examiner

*Primary Examiner*—Edward J. Glick
*Assistant Examiner*—Elizabeth Keaney
(74) *Attorney, Agent, or Firm*—Schiff Hardin LLP

(57) ABSTRACT

An X-ray diagnostics device for mammography examinations has an arm for an X-ray tube and a subject table as well as a compression plate arranged between the X-ray tube and the subject table, the compression plate being connected to the arm and being displaceable along it to compress a female breast. The arm is rotatable around a horizontal shaft, and the shaft is secured to a mount that is laterally displaceable. The mount is displaceably attached to a lifting arrangement connected to the stand that is height-adjustable. A control device accepts output signals from position sensors that indicate the height and lateral positions of the arm as well as from a synchro system that indicates the rotational angle of the arm, to control displacement arrangements the arm such that a rotation of the arm around an axis that can be arbitrarily selected along the longitudinal axis of the stand that is substantially aligned with the center axis of the compressed breast.

3 Claims, 4 Drawing Sheets

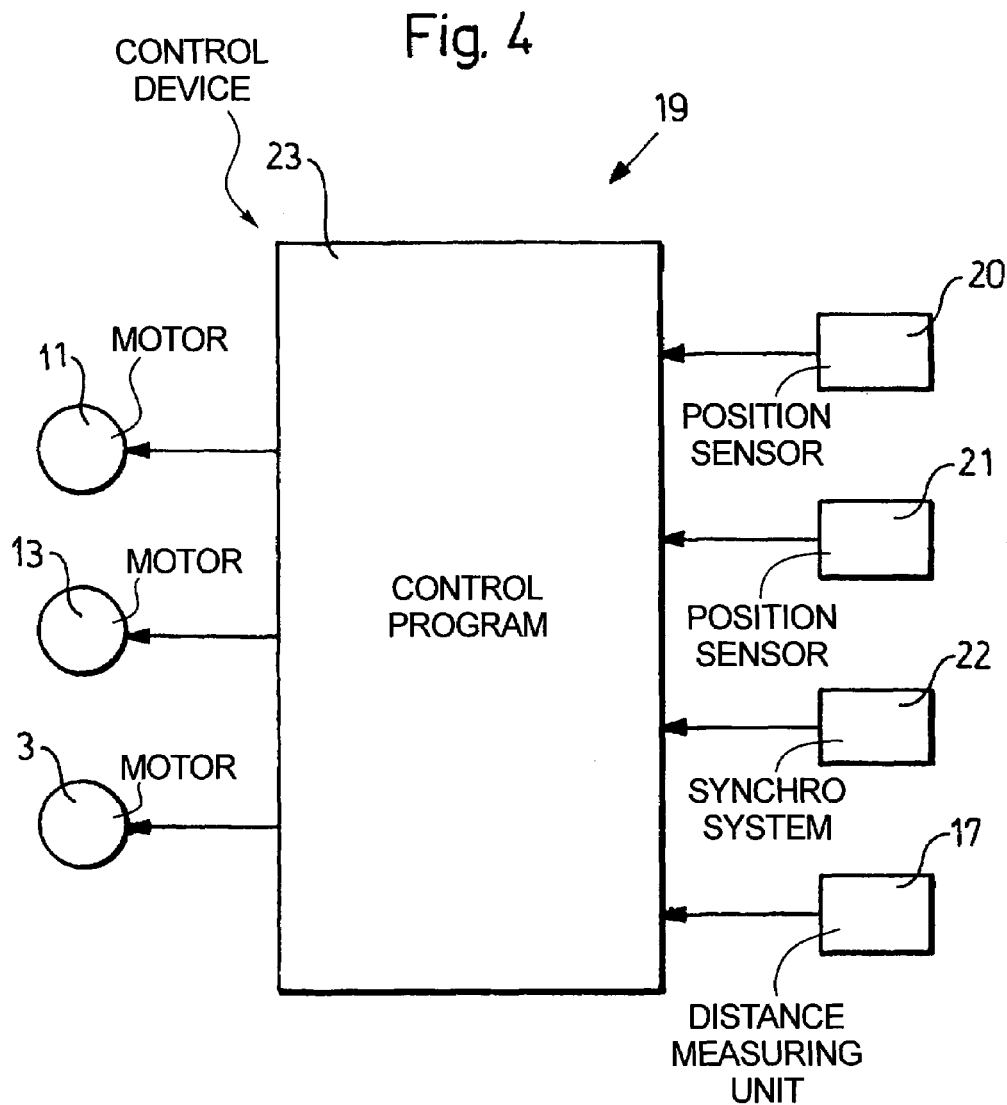

X-RAY DIAGNOSTIC DEVICE FOR MAMMOGRAPHY EXAMINATIONS

BACKGROUND OF THE INVENTION

1. Field of the Invention

The present invention is directed to an X-ray diagnostic device for mammography examinations having an arm for an X-ray tube and a subject table as well as a compression plate arranged between the X-ray tube and the subject table, the compression plate being connected to the arm and being displaceable along it, wherein the arm can be rotated around a horizontal shaft and is height-adjustable along an imaginary longitudinal axis of a stand.

2. Description of the Prior Art

An X-ray diagnostic device of this type is disclosed in European Application Patent 0 370 089. In this device, the rotational axis of the arm lies outside the center of gravity of the arm. In order for the arm with the X-ray tube, the compression plate and the subject table to be able to be rotated around the rotational axis, the free end of the rotational axis is provided with a gearwheel rigidly connected to this end that is driven by a comparatively strong and thus comparatively large, motor. A pneumatic spring device serves for additional weight compensation of the arm. The vertical displacement of the arm ensues with a motor and a toothed rack that are arranged separately from the rotational device of the arm.

In a routine examination of a breast of a patient, a first vertical exposure and subsequently a second exposure are made, with the arm being rotated by an angle between 45° and 60° between the two exposures. An exposure when the arm has been turned by approximately 90° also can be made in conjunction with a further examination. In order to avoid the patient having to step aside given rotation of the arm from the first exposure position into the second exposure position, the extension of the imaginary center axis of the rotational axis is arranged in the device disclosed in European Application 0 370 089 so that it lies immediately above the subject table. The distance between the subject table and the center axis is fixed, which means that most patients must undertake a certain lateral position correction when changing from a vertical exposure position into a lateral exposure position. Only a few patients have a breast size for which this device is suitable without such a correction, so that the imaginary center axis lies in axial alignment with the imaginary center axis of the compressed breast.

SUMMARY OF THE INVENTION

An object of the present invention is to provide an X-ray diagnostic device for mammography examinations of the type initially described wherein the rotary motions of the arm can be implemented simply, so that the arm can be rotated around an isocenter adapted to the patient from one exposure position into another exposure position with the desired rotational angle, and such that the patient can remain in position regardless of the breast size.

This object is achieved in an X-ray diagnostic device of the type initially described wherein the arm is rotatable with a first displacement arrangement around the horizontal shaft, the shaft is secured to a mount that is laterally displaceable with a second displacement arrangement, as a result of which the arm is laterally displaceable. The arrangement mount is displaceably attached to a lifting arrangement connected to the stand, the lifting arrangement is height-adjustable with a third displacement arrangement. A control device is operable, using a control program that accepts output signals of position sensors that indicate the height and lateral positions of the arm as well as from a synchro system that indicates the rotational angle of the arm. The control device controls the second and third displacement arrangements for the displacement of the arm laterally and in height as well as the first displacement arrangement for the rotation of the arm such that a rotation of the arm around an axis that can be arbitrarily selected along the longitudinal axis of the stand is enabled. In particular, the first and second displacement arrangements preferably are low-power, inexpensive motors that can rotate the arm around the selective axis with the assistance of the control device. Due to the compact structure of the aforementioned arm arrangement, a weight compensation device is not needed for the rotary movements of the arm, since the rotary movements always ensue in the proximity of the center of gravity of the arm.

In an embodiment of the X-ray diagnostics device of the invention, the imaginary axis lies at a distance from the subject table is half the distance between the subject table and the compression plate when the compression plate is in a compression position. The choice of rotating the arm around the selected axis assures that the patient need not be repositioned when changing the exposure angle, regardless of the breast size.

DESCRIPTION OF THE DRAWINGS

FIG. 4 is a block circuit diagram of a control device of the arm arrangement.

DESCRIPTION OF THE PREFERRED EMBODIMENTS

Figure 1:
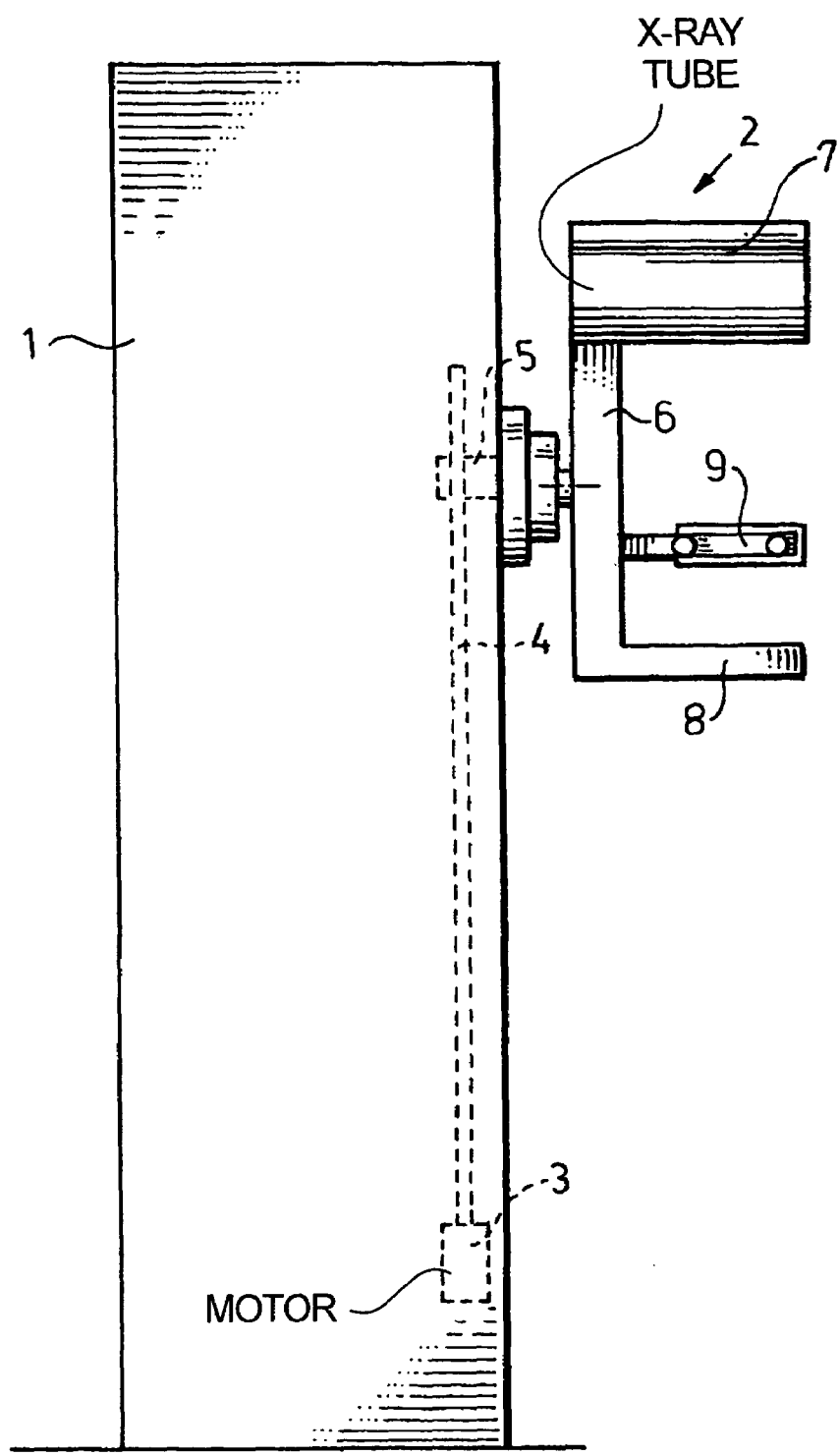
FIG. 1 is a side view of an X-ray diagnostics device having an arm arrangement of the invention.

FIG. 1 schematically shows an X-ray diagnostics device for mammography examinations, i.e. a mammography device, having a stand 1 that carries an arm arrangement 2 that shall be described later. The arm arrangement 2 is height-adjustable with the assistance of a motor 3 and a screw 4 having one end connected to a part 5 that is rigidly arranged at the arm mechanism.

Figure 2:
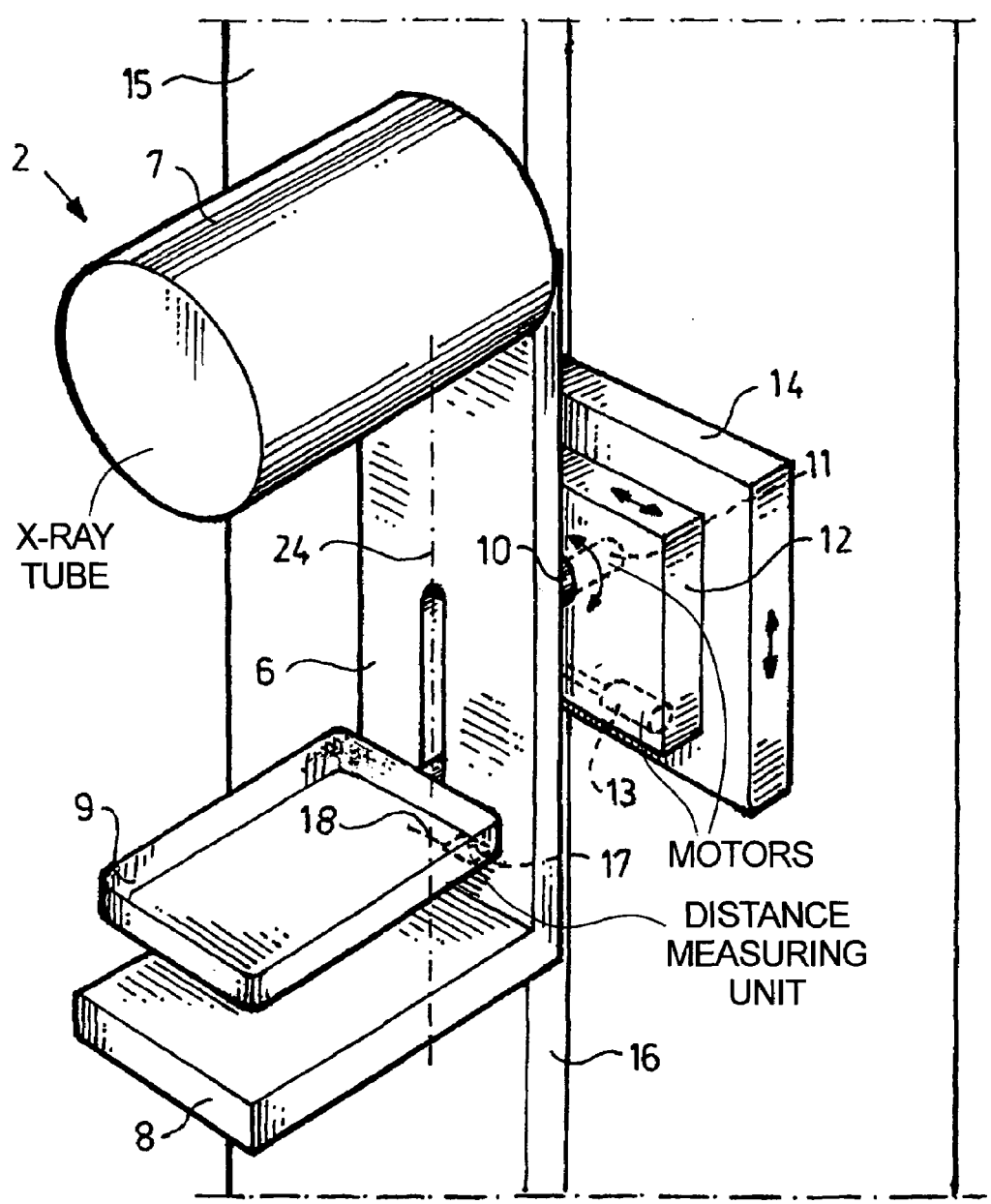
FIG. 2 is a perspective view of an arm arrangement according to FIG. 1.

FIG. 2 shows the arm arrangement 2, composed of an arm 6, an X-ray tube 7 arranged at the arm 6 and a subject table 8 as well as a compression plate 9 arranged between the X-ray tube 7 and the subject table 8, the compression plate 9 is connected to the arm 6 and is displaceable along it. FIG. 2 also shows that the arm 6 of the arm arrangements is rotatable around a horizontal shaft 10 with the assistance of a motor 11. The shaft 10 is secured to a lateral carriage 12, i.e. a carriage that is laterally displaceable with the assistance of a motor 13. As a result, the arm 6 is also laterally displaceable. The carriage 12 is displaceably arranged at a lifting element 14 that is connected via the aforementioned part 5 to the screw 4 for displacing the lifting element 14 and, thus, for displacing the arm arrangement 2 in height. FIG. 2 also shows the end face 15 of the mammography device. This end face 15 is provided with a slot 16 in which the part 5 proceeds and along which the arm mechanism 2 is therefore height-displaceable.

Figure 3:
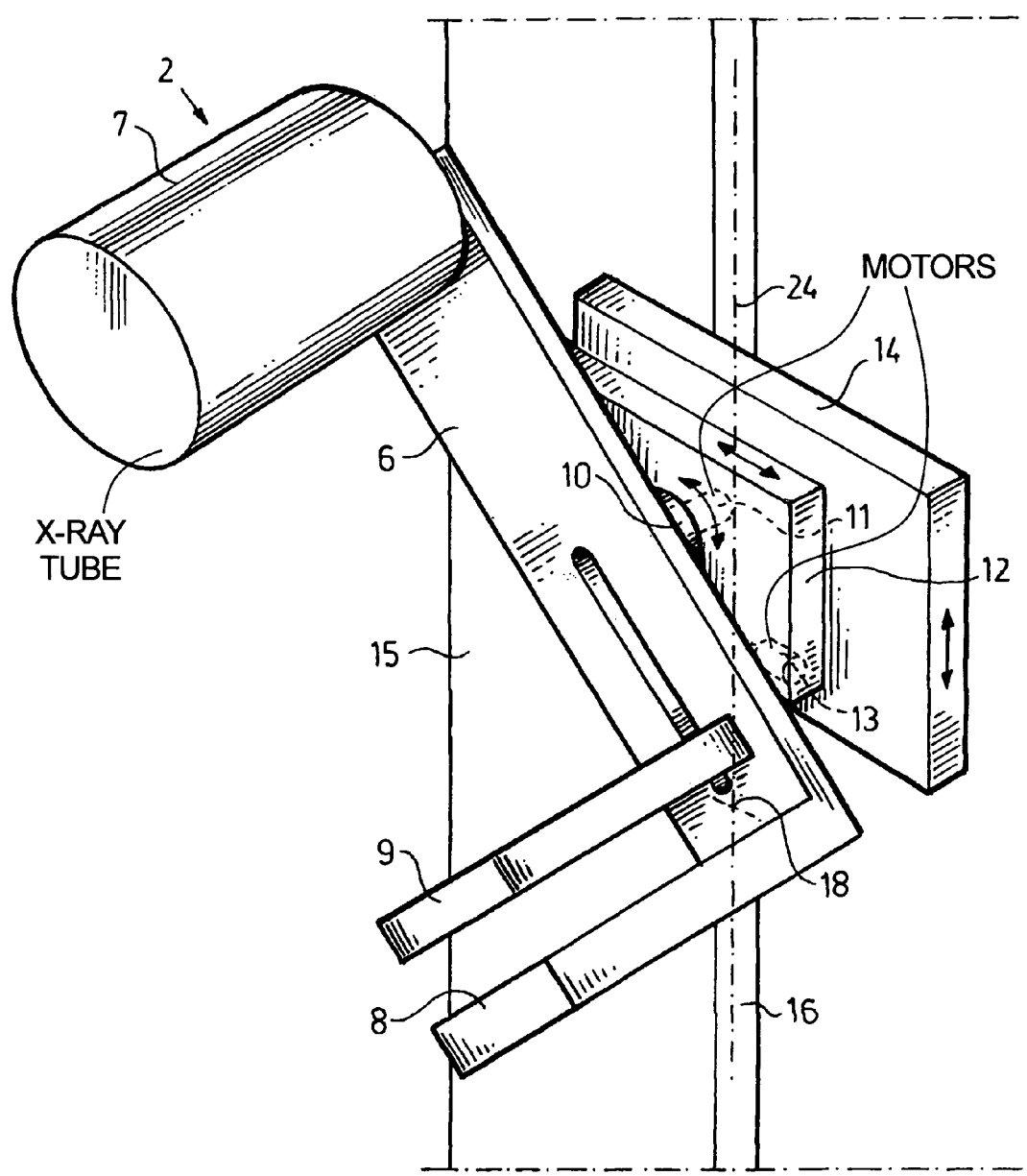
FIG. 3 is a perspective view of an arm arrangement according to FIGS. 1 and 2 wherein the arm is shown in an exposure position different from that shown in FIG. 2.

Before an examination of a breast of a patient (not shown), the arm arrangement 2 is shifted along a longitudinal axis 24 of the stand 1 into a position wherein the subject table 8 assumes a position suitable for the patient. (The longitudinal axis 24 is definable within the stand 1, but is not a separate physical components). The longitudinal axis 24 preferably proceeds parallel to the slot 16. With the compression plate 9, the breast is now pressed against the subject table 8 until an optimum compression of the breast has been obtained for an exposure, whereupon a vertical exposure of the breast is implemented. The compression plate 9 is provided with a distance-measuring unit 17 that measures the distance from the subject table 8 in this position. The distance-measuring unit 17, which preferably is attached to that end of the compression plate 9 that is directed toward the arm 6, shall be described below. The patient is released from the compressed position after a first vertical exposure of the breast, and the arm 6 is rotated from the described, vertical exposure position into a second exposure position having an angle of 45° through 60° from the first exposure position. Such a second exposure position is shown in FIG. 3. The arm 6 is then rotated around an axis 18 that lies at a distance from the subject table 8 that corresponds to half the distance between the subject table 8 and the compression plate 9 when the compression plate 9 is in its above-described compression position. Like the axis 24, the axis 18 is definable but is not a separate physical component.

The position of the axis 18 is determined with the assistance of the distance-measuring unit 17 and a control device 19, which shall be described below.

The rotation of the arm 6 around the axis 18 ensues by a simultaneous combination of all motion possibilities of the arm mechanism 2, i.e. partly by rotating the arm 6 around the shaft 10, partly by a height displacement of the arm 6 and partly by a lateral displacement of the arm 6.

FIG. 4 shows a control device 19 for the arm arrangement 2 in the form of a schematic block circuit diagram. The control device 19 is composed of a position sensor 20, which indicates the height position of the arm 6, of a position sensor 21 that indicates the lateral position of the arm, and a synchro system 22 that indicates the rotational angle of the arm 6. The sensors 20, 21 and the synchro system 22 are not shown in other figures, however, they can be placed at strategic locations at the mammography device. The control device 19 is also includes the distance measuring unit 17 described in conjunction with FIG. 2. The control device 19 also has a control program 23 that—when the arm 6 is rotated—is continuously supplied with signals from the sensors 20, 21 and from the synchro system 22 that respectively correspond to the momentary height, lateral and rotary positions of the arm 6. The control program 23 also stores input signals from the distance-measuring unit 17 that correspond to the distance between the subject table 8 and the compression plate 9. The control program 23 divides the value of the input signal by two and thus calculates the position of the horizontal axis 18 around which the arm 6 is to be turned. The horizontal axis 18 always lies in axial alignment with the center axis of the breast when it is in a compression position. The control program 23 processes the supplied information. The result of the processed information is then supplied to the motor 11 for rotating the arm 6, to the motor 13 for the lateral displacement of the carriage 12 as well as to the motor 3 for the vertical displacement of the arm 6. A control device 19 of this type is disclosed in U.S. Pat. No. 4,109,059 and therefore need not be described in greater detail. The distance-measuring unit 17 described herein is not disclosed in conjunction with the control device according to this United States patent.

Because the control device 19 can individually calculate an optimum axis 18 around which the arm 6 can be rotated for each patient in the described way, a repositioning of the patient from a vertical exposure position into a desired, lateral exposure position is not necessary, regardless of the size of the beast. The axis 18 is always applied along the longitudinal axis 24 of the stand 1 that proceeds parallel to the slot 16.

Although modifications and changes may be suggested by those skilled in the art, it is the intention of the inventors to embody within the patent warranted hereon all changes and modifications as reasonably and properly come within the scope of their contribution to the art.

We claim:

1. An X-ray diagnostic device for mammography examinations, comprising:
   an X-ray tube, a subject table to support a female breast thereon and a compression plate attached to an arm, said compression plate being displaceable along said arm between said X-ray tube and said subject table and thus compressing the breast on the subject table to a compressed position;
   a stand having a vertical longitudinal axis;
   a first displacement arrangement, a second displacement arrangement and a third displacement arrangement;
   a lifting element displaceable in said stand along said longitudinal axis by said first displacement arrangement;
   a mount attached to said lifting element, said mount having a horizontal shaft to which said arm is attached;
   said mount and said arm being laterally displaceable relative to said lifting element by said second displacement arrangement and said arm being rotatable around said shaft by said third displacement arrangement;
   a first position sensor which detects, and emits an output signal corresponding to, a height of said lifting element along said longitudinal axis;
   a second position sensor which detects, and emits an output signal corresponding to, a lateral position of said mount relative to said lifting element;
   a synchro system which detects, and emits an output signal corresponding to, a rotational angle of said arm relative to said shaft;
   a distance meter disposed at said compression plate that detects, and emits an output signal corresponding to, a distance of said compression plate from said subject table; and
   a control unit, supplied with the respective outputs from said first and second position sensors, said synchro system and said distance meter, for controlling said first, second and third displacement arrangements dependent on said outputs, to rotate said arm around an arbitrarily selectable spatial axis along said longitudinal axis that is substantially aligned with a center axis of the breast in the compressed position.

2. An X-ray diagnostic apparatus as claimed in claim 1 wherein said compression plate is displaceable into a compression position, and wherein said control unit sets said spatial axis at a distance from said subject table equal to half a distance between said subject table and said compression plate in said compression position.

3. An X-ray diagnostic apparatus as claimed in claim 1 wherein said compression plate has a first plate end and a second plate end, said first plate end being disposed closer to said arm than said second plate end, and wherein said distance sensor is disposed at said first plate end of said compression plate.

* * * * *